United States Patent
Jia et al.

(10) Patent No.: US 12,070,518 B2
(45) Date of Patent: Aug. 27, 2024

(54) METHOD FOR PRODUCING PET DENTAL TREAT

(71) Applicant: Blue Buffalo Enterprises, Inc., Wilton, CT (US)

(72) Inventors: Tiandong Jia, Belle Mead, NJ (US); Jie Sun, Plymouth, MN (US); Christine S. t. Ng, Minneapolis, MN (US)

(73) Assignee: Blue Buffalo Enterprises, Inc., Wilton, CT (US)

( * ) Notice: Subject to any disclaimer, the term of this patent is extended or adjusted under 35 U.S.C. 154(b) by 231 days.

(21) Appl. No.: 17/869,261

(22) Filed: Jul. 20, 2022

(65) Prior Publication Data
US 2024/0024225 A1  Jan. 25, 2024

(51) Int. Cl.
*A61K 8/9794* (2017.01)
*A23K 10/18* (2016.01)
(Continued)

(52) U.S. Cl.
CPC ............ *A61K 8/9794* (2017.08); *A23K 10/18* (2016.05); *A23K 10/35* (2016.05); *A23K 20/105* (2016.05); *A23K 20/163* (2016.05); *A23K 20/174* (2016.05); *A23K 20/189* (2016.05); *A23K 20/22* (2016.05); *A23K 40/25* (2016.05); *A23K 40/30* (2016.05); *A23K 50/40* (2016.05); *A61K 8/0216* (2013.01); *A61K 8/19* (2013.01);
(Continued)

(58) Field of Classification Search
CPC ........ A23K 1/00; A23K 1/004; A23K 424/58; A23K 426/89; A23K 426/94; A23K 426/275

USPC ............................ 424/439, 442, 401; 426/89
See application file for complete search history.

(56) References Cited

U.S. PATENT DOCUMENTS

D532,582 S  11/2006  Kelsoe et al.
D603,136 S  11/2009  Unlu et al.
(Continued)

FOREIGN PATENT DOCUMENTS

DE  102015107453  8/2016
KR  20130005449  9/2013

OTHER PUBLICATIONS

Purina DentaLife daily Oral Care Chew Treats for Small & Medium Dogs, Aug. 31, 2022 https://www.purina.com/dentalife/dogs/dental-chews/daily-oral-care-medium-small-dogs.

*Primary Examiner* — Walter E Webb
(74) *Attorney, Agent, or Firm* — Jordan IP Law, PLC; Annette M. Frawley, Esq.

(57) ABSTRACT

A pet dental treat includes an outer shell constituting a dense, solid shell which keeps the dog occupied while the dog's teeth sink into a soft, chewy porous inner core, potentially coated on exposed surface(s) such as with a bio-active compound, to scrape tartar and remove plaque from the dog's teeth, including hard-to-reach teeth, thereby helping to maintain the oral health of the dog while also reducing bad breath. The pet dental treat has a cross-section visually resembling a tooth and includes a longitudinal slot defining an integral pocket having in-turned retaining elements at an entrance to the slot, with the pocket provided to selectively retain a functional, edible additive insert, such as a vitamin, medicinal item or the like insert, to be given to the pet, with the retaining elements preventing the edible insert from inadvertently falling out of the pocket.

19 Claims, 2 Drawing Sheets

(51) Int. Cl.
| | |
|---|---|
| *A23K 10/35* | (2016.01) |
| *A23K 20/105* | (2016.01) |
| *A23K 20/163* | (2016.01) |
| *A23K 20/174* | (2016.01) |
| *A23K 20/189* | (2016.01) |
| *A23K 20/22* | (2016.01) |
| *A23K 40/25* | (2016.01) |
| *A23K 40/30* | (2016.01) |
| *A23K 50/40* | (2016.01) |
| *A61K 8/02* | (2006.01) |
| *A61K 8/19* | (2006.01) |
| *A61K 8/365* | (2006.01) |
| *A61K 8/65* | (2006.01) |
| *A61K 8/66* | (2006.01) |
| *A61K 8/73* | (2006.01) |
| *A61K 8/9789* | (2017.01) |
| *A61K 8/98* | (2006.01) |
| *A61K 8/99* | (2017.01) |
| *A61Q 11/00* | (2006.01) |

(52) U.S. Cl.
CPC ............... *A61K 8/365* (2013.01); *A61K 8/65* (2013.01); *A61K 8/66* (2013.01); *A61K 8/731* (2013.01); *A61K 8/9789* (2017.08); *A61K 8/986* (2013.01); *A61K 8/99* (2013.01); *A61Q 11/00* (2013.01); *A61K 2800/92* (2013.01)

(56) References Cited

U.S. PATENT DOCUMENTS

| | | |
|---|---|---|
| 8,771,775 B2 | 7/2014 | Axelrod et al. |
| 9,713,338 B2 | 7/2017 | Mahe |
| 10,159,266 B2 | 12/2018 | Xu |
| 10,166,186 B2 | 1/2019 | Brunel et al. |
| 2006/0188611 A1 | 8/2006 | Unlu et al. |
| 2007/0098841 A1 | 5/2007 | Keehn et al. |
| 2009/0235872 A1 | 9/2009 | Filipi et al. |
| 2011/0052662 A1 | 3/2011 | Weiss |
| 2011/0076363 A1* | 3/2011 | Niehues ............... A23K 40/20 426/89 |
| 2011/0139087 A1 | 6/2011 | Lang et al. |
| 2014/0186276 A1* | 7/2014 | Mahe ............... A01K 15/026 426/94 |
| 2014/0290587 A1 | 10/2014 | Dixon |
| 2015/0373950 A1* | 12/2015 | Spring ............... A01K 15/026 426/282 |
| 2016/0143320 A1 | 5/2016 | Mahe et al. |
| 2021/0235725 A1 | 8/2021 | Schennink et al. |
| 2022/0087804 A1 | 3/2022 | Werdelin et al. |

* cited by examiner

METHOD FOR PRODUCING PET DENTAL TREAT

FIELD OF THE INVENTION

The invention generally pertains to the art of edible pet products and, more particularly, to a method for producing a pet dental treat including an outer shell encapsulating a porous core to establish a dual texture dog chew treat, with the outer shell being formed with an integral pocket for selectively retaining an additional edible insert.

BACKGROUND OF THE INVENTION

Pet owners often feed treats to their pets to show affection, create interactive moments with their pets, or reward their pets. As consumers are increasingly treating their pets like family members, the oral health of these domestic animals has become of particular concern. With this being recognized by manufacturers, various pet treats specifically formulated to promote the oral health of pets, particularly dogs, have been made readily available to consumers. Certain known pet dental treats include hard outer bodies, e.g., hide or bone, and a softer edible core portion. Tooth plaque and tarter are removed as portions of the product scrape against the animal's teeth while the treats are being chewed.

Although available pet treats specifically intended for dental hygiene are widely known, there are still improvements to be made in this field, particularly to further improve oral cleaning attributes of the products, provide products which are longer lasting and specifically formulated to be more digestible, and also enhance the versatility of the products by providing for the ability to also present functional, edible additives, such as vitamins, medicinal items or the like, to pets. With the above in mind, it is desired to provide a method for mass producing pet dental chews treats, particularly employing a co-extrusion or molding process to establish a dual texture product, with each pet treat being formulated for ease of digestion and integrally formed with structure to selectively retain an additional edible insert.

SUMMARY OF THE INVENTION

The present invention is concerned with a method for producing pet dental treats, particularly for dogs. In one form of the invention, a co-extrusion process is employed to produce product ropes having a dual texture, i.e., a long-lasting outer, chewable shell with a soft, chewy porous core. The rope is fed to a cutter assembly which can be configured to produce products of predetermined length, such as slices, sticks or logs. In another form of the invention, the dental treats are formed through a molding process. In either form of production, the outer shell constitutes a dense, solid shell which keeps the dog occupied while the dog's teeth sink into the soft, chewy porous core to scrape tartar and removes plaque from the dog's teeth, including hard-to-reach teeth and along gumlines, thereby helping to maintain the oral health of the dog while also reducing bad breath. Regardless of the length of the product, the pet dental treat has a cross-section visually resembling a tooth, which not only provides an indication of the product's dental function but advantageously enables the inclusion of a longitudinal slot defining an integral pocket including in-turned retaining elements at an entrance to the slot. This pocket is provided to selectively retain one or more functional, edible additive inserts, such as vitamins, medicinal items or the like inserts, to be given to the pet, with the retaining elements preventing the edible insert(s) from inadvertently falling out of the pocket.

Although the pet dental treat of the invention can be made from various ingredients, it is preferred that the outer shell constitute a dense, grain-based solid which will be long lasting and highly digestible. For instance, the outer shell can include rice flour, potato flour, gelatin, glycerin, pea starch, cultured whey, cellulose, citric acid and salt. On the other hand, the chewy porous core can includes rice flour, potato starch, gelatin, glycerin, cultured whey, citric acid and salt. Meat may also be employed in forming the outer shell and/or inner core. In any case, it is intended that the entire product contains no artificial colors, artificial flavors or artificial preservatives so as to establish an overall healthy, highly digestible, long lasting pet treat having dental cleaning functionality. In certain embodiments of the invention, the exposed surfaces of the soft, chewy porous (permeable) core can provide a suitable carrier for active ingredients in liquid form to be infused, such as through a coating operation. For instance, a coating of heat sensitive bio-active compounds, such as probiotics, enzymes such as papain, antioxidants, antimicrobials, vitamins, calcium peroxide, flavors, calcium chelating agents, plant or plant extracts, can be employed. To avoid deactivation during process stages of higher temperature, the heat-labile ingredients can be applied via a low temperature coating to the pet treat after the product has been extruded or molded.

Additional objects, features and advantages of the invention will become more readily apparent from the following description of preferred embodiments of the invention when taken in conjunction with the drawings.

DETAILED DESCRIPTION OF THE INVENTION

Figure 1:
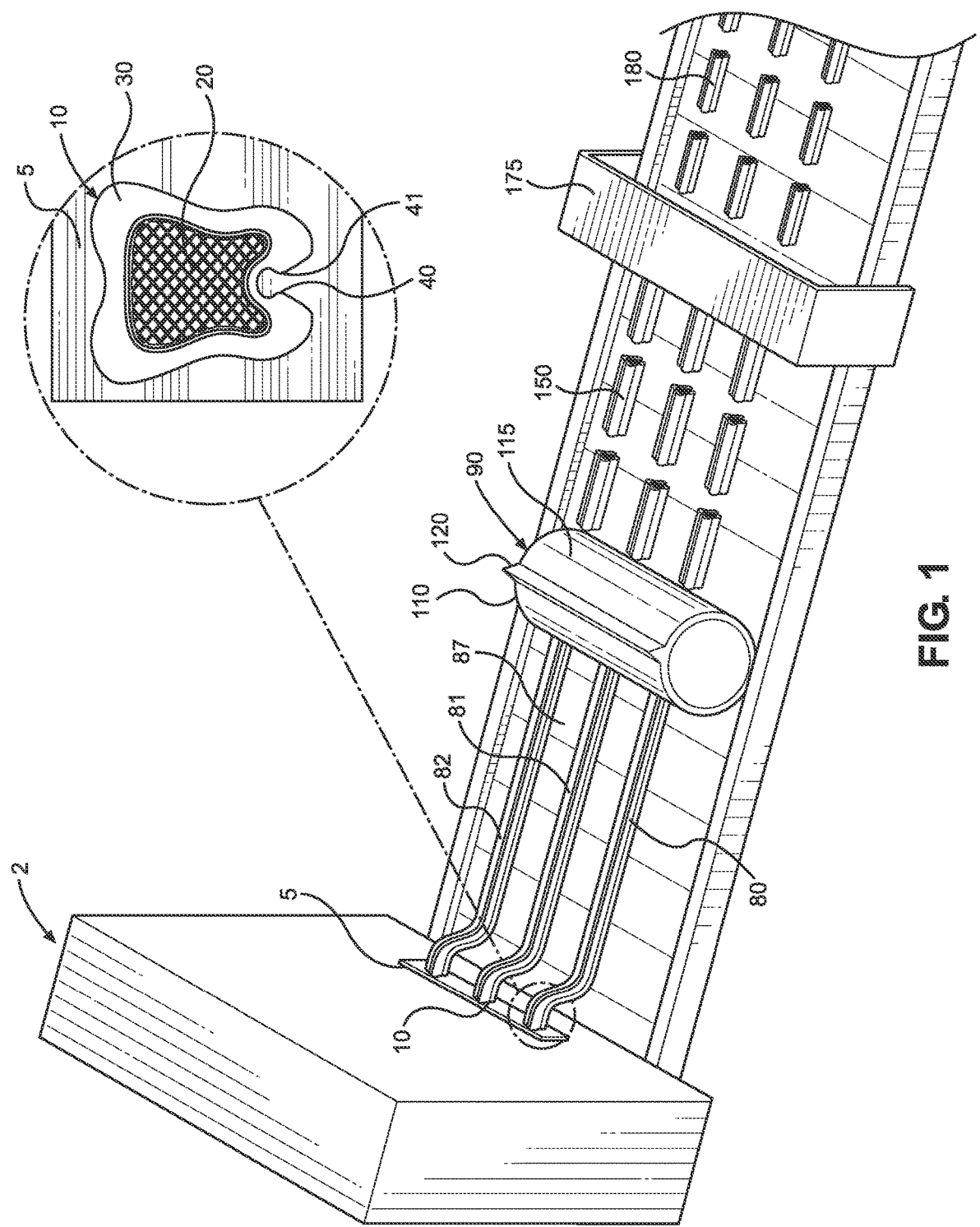
FIG. 1 is a perspective view of a portion of a manufacturing line for producing pet dental treats in accordance with the invention.

As indicated above, the product of the invention can be made employing various production techniques, including co-extrusion and molding processes. FIG. 1 schematically illustrates a portion of an exemplary manufacturing line for the automated mass production of pet dental treats in accordance with the invention. This arrangement employs a multi-row co-extruder 2 including a die plate 5 having a plurality of laterally spaced heads or dies, one of which is indicated at 10. As shown in the enlarged view, each die 5 is defined by a port or an opening in die plate 5, with the co-extrusion opening having an outer peripheral shape resembling a tooth (see enlarged view). Of course, other arrangements are equally applicable, such as die plate 5 threadably or otherwise receiving various selectively replaceable die inserts to establish the requisite opening. In the embodiment shown, the co-extrusion opening includes a central extrusion region 20 and an outer extrusion region 30 which surrounds central extrusion region 20. Important in connection with an aspect of the invention for reasons which will be detailed herein, outer extrusion region 30 is integrally formed with in-turned retaining elements 40 and 41 along a longitudinal slot (not labeled but discussed further below in connection with FIG. 2). Again, for exemplary purposes, extruder 2 is shown to form a plurality of elongated, laterally spaced extrudate rows deposited in the form of continuous ropes 80-82 onto a common conveyor 87, with each rope 80-82 having a cross-section visually resembling a tooth.

Downstream of extruder 2 is provided a cutting assembly which is generally indicated at 90 extending across conveyor 87. Cutting assembly 90 includes a roller 110 having an associated motor driven drive shaft (not shown) for rotating roller 110 and an outer surface 115 from which project one or more cutting members, such as a blade indicated at 120. With this exemplary arrangement, each rope 80-82 passing beneath roller 110 upon moving conveyor 87 will be cut by the one or more cutting members in forming individual, tooth-shaped (in cross-section) intermediate products 150. The length of each intermediate product 150 will depend on various factors, including the speed of extrusion and conveyance, the rotational speed of roller 110 and the number of cutting members 120 provided circumferentially spaced about roller 110. Overall, the length can vary significantly but, in most preferred forms of the invention, the resulting pet treat has a length in a range of approximately 1.25-18 cm.

After being cut to a desired length, the intermediate products 150 need to be dried. Although drying could proceed under ambient conditions, FIG. 1 illustrates the inclusion of a dryer unit 175 downstream of cutting assembly 90, with conveyor 87 directing intermediate products 150 through dryer unit 175 in producing the final pet treats 180 having tooth-shaped bodies in cross-section. At this point, pet treats 180 can be transported to a further downstream location where they are packaged for shipping and consumer sale.

Figure 2:
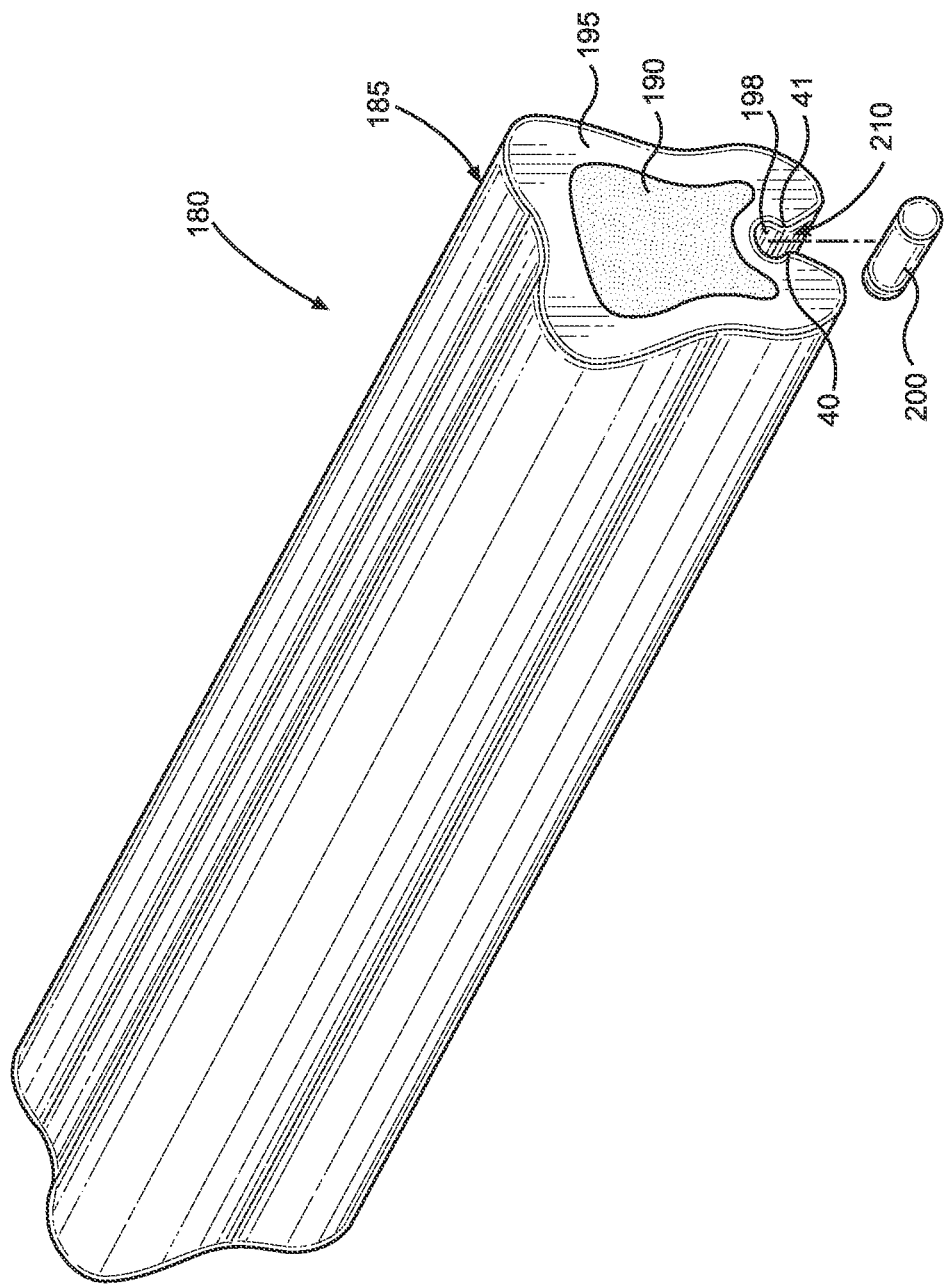
FIG. 2 is a perspective view of a pet dental treat according to the invention.

A pet treat 180 produced in accordance with the invention is illustrated in FIG. 2. As clearly illustrated, the pet treats 180 of the invention have a tooth-shaped cross-sectional body generally indicated at 185 including a soft, chewy inner core 190 surrounding by a dense, solid outer shell 195. Certainly, the dense, solid characteristics of outer shell 195 and the soft, chewy characteristics of core 190 can be defined in various ways. By way of example, dense, solid outer shell 195 is reminiscent of a rawhide, having a hardness (Force kg) in the range of 20-120 and a preferred target of 60, as well as a flexibility (Force Ascending Slope Kg/sec) in the range of 20-120 and a preferred target of 60. On the other hand, core 190 is more like a sponge, having a hardness (Force Kg) in the range of 3-20 and a preferred target of 15, along with a flexibility (Force Ascending Slope Kg/sec) in the range of 1-45 and a preferred target of 10. For the sake of completeness, the bend analysis (3-point) was performed with a TA-HD plus instrument equipped with a 250 Kg load cell and a 3 mm thick 450 chiseled end blade. The bend upright supports were set to a 6 cm gap. The associated blade traveled a distance of 20 mm at a rate of 5 m/sec with a 10 g trigger start.

Importantly, outer shell 195 has integrally formed therewith the in-turned retaining elements 40 and 41 along a longitudinal slot (not separately labeled) establishing a pocket 198 defined, at least in part, by retaining elements 40 and 41. This overall configuration is important in providing added versatility to pet treat 180 by enabling a functional, edible additive, such as a vitamin, medicinal item or the like insert 200, to be given to the pet by pushing insert 200 past retaining elements 40 and 41 and into pocket 198. As clearly shown in this figure, pocket 198 is laterally restricted at an entrance region or opening 210 by retaining elements 40 and 41 such that retaining elements 40 and 41 function to prevent edible insert 200 from inadvertently falling out of pocket 198 after insertion, while still enabling a pet to access insert 200. As indicated above, edible insert 200 can be constituted by a wide range of items, including medicinal items, vitamins, palatability enhancers, digestion additives like probiotics, enzymes, and mouth surface effective compositions like polyphosphates, any of which can be in pill, capsule, gummy, paste or other form. Depending on the length of the slot forming pocket 198, multiple inserts can be provided in a single pet treat 180 which can be extremely convenient if a pet must receive daily medicines or other supplements. Any insert 200 may be added during the production process and therefore sold as a variety of pet treat 180 or, preferably, pocket 198 exists to enable consumers to individually tailor pet treats 180 for consumption by their pets.

As indicated above, pet treats 180 can be produced in various lengths without departing from the invention. In addition, the particular composition of pet treats 180 can also vary. A preferred composition of the invention is presented below, with the listed percentage ranges and most preferred or target range percentages (by weight) before (Table 1) and after (Table 2) drying.

TABLE 1

| Ingredient description | Shell | | Core | |
| --- | --- | --- | --- | --- |
| | Range | Target Range | Range | Target Range |
| Rice Flour | 10-35% | 21-25% | 12-37% | 24-28% |
| Potato Flour | 10-25% | 17-21% | 8-25% | 12-16% |
| Potato Starch | 5-10% | 8-10% | 6-20% | 12-16% |
| Gelatin & Ground Pea | 0.10-10% | 5-7% | 0.10-10% | 3-6% |
| Pea Starch | 0.10-10% | 1.5-3.5% | 0.10-10% | 4.5-6.5% |
| Cultured Whey | 0.10-1% | 0.2-0.7% | 0.10-1% | 0.2-0.7% |
| Citric Acid | 0.10-3% | 0.5-2% | 0.10-3% | 0.5-2% |
| Salt | 0.10-1% | 0.1-0.5% | 0.10-1% | 0.1-0.5% |
| Chicken Meal | 2.5-10% | 1.5-3.5% | 2.5-10% | 2.5-4.5% |
| Glycerin | 1-15% | 6.5-10.5% | 1-15% | 7-11% |
| Vegetable oil | 1-5% | 1.25-2.5% | 1-5% | 1.25-2.5% |
| Water | 11-45% | 20-28% | 11-45% | 15-22% |
| Total | | 100.0% | | 100.0% |

TABLE 2

| Ingredient description | Shell | | Core | |
|---|---|---|---|---|
| | Range | Target Range | Range | Target Range |
| Rice Flour | 10-44% | 24.5-29% | 12-45% | 25.5-31% |
| Potato Flour | 10-31% | 20-24% | 8-31% | 12.5-18% |
| Potato Starch | 5-12% | 8.5-13% | 6-25% | 12.5-17% |
| Gelatin & Ground Pea | 0.10-12% | 5-8% | 0.10-12% | 3-6% |
| Pea Starch | 0.10-12% | 2-4% | 0.10-12% | 5-7% |
| Cultured Whey | 0.10-1% | 0.3-0.8% | 0.10-1% | 0.3-0.8% |
| Citric Acid | 0.10-4% | 0.7-2.5% | 0.10-4% | 0.7-2.5% |
| Salt | 0.10-1% | 0.15-0.55% | 0.10-1% | 0.15-0.55% |
| Chicken Meal | 2.5-12% | 2-4% | 2.5-12% | 2.5-5% |
| Glycerin | 1-19% | 7-11% | 1-19% | 7.5-11.5% |
| Vegetable oil | 1-6% | 1.5-3% | 1-6% | 2-4.5% |
| Water | 10-14% | 11-13% | 10-14% | 11-13% |
| Total | | 100.0% | | 100.0% |

In this example, the ropes 80-82 are co-extruding a pre-blend of dry ingredients with a heated liquid addition to establish an extrusion exit moisture range of approximately 25-30% at a temperature of approximately 180-210° F. and an exit pressure of approximately 500-1100 psi. Ropes 80-82 are preferably in the range of approximately 2.5-5 cm in diameter and are cut to preferred lengths in the range of approximately 1.25-18 cm. After the drying process, outer shell 195 of pet treat 180 has a moisture in the range of 8-12% while inner core 190 has a moisture of 2-3 times that of outer shell 195, with dryer unit 175 being employed to expedite the drying process. Optionally, another dryer (not shown) can be provided upstream of cutting assembly 90 for this purpose.

The invention also contemplates taking advantage of the soft, chewy porous nature of core 190 to potentially apply one or more infusible coatings (not separately shown or labeled) to the exposed surfaces of inner core 190. For example, one or more coatings containing bio-active compounds, including probiotics, enzymes such as papain, antioxidants, antimicrobials, vitamins, calcium peroxide, flavorings, calcium chelating agents, plant compounds or plant extracts, or the like can be applied to inner core 190, preferably in liquid form for easy infusion. A flavored coating could be employed to enhance product appealability, such as a meat-based coating. As the heating conditions employed for extrusion or injection molding processes would be detrimental to heat-labile active ingredients, the coating can be applied after the extrusion or molding process, i.e., after the body sufficiently cools to a temperature which will not deactivate the heat-labile active ingredients.

Although described with reference to preferred embodiments of the invention, it should be understood that various changes and/or modifications can be made to the invention without departing from the spirit thereof. For instance, various cutting assemblies known in the art could be equally employed, such as linear or guillotine, ultrasonic or the like cutting assemblies. Instead, the invention is only intended to be limited by the scope of the following claims.

We claim:

1. A method of producing pet dental treats comprising forming a body with a soft, chewy, porous inner core and an outer shell surrounding the porous core, said outer shell being tooth-shaped in cross-section and having integrally formed therewith in-turned retaining elements at an entrance region to a longitudinally extending slot, with the retaining elements defining, at least in part, a pocket of the slot.

2. The method of claim 1, further comprising: inserting an edible insert into the pocket by pushing the edible insert past the retaining elements and into the pocket, with the retaining elements functioning to prevent the edible insert from inadvertently falling out of pocket after insertion.

3. The method of claim 2, wherein the edible insert comprises a medicinal item, a vitamin, a supplement, a palatability enhancer, a digestion additive or a mouth surface effective composition.

4. The method of claim 3, wherein the edible insert takes the form of a pill, capsule, gummy, or paste.

5. The method of claim 1, wherein forming the body includes:
   extruding the body in the form of at least one rope;
   directing the at least one rope to a cutting assembly which cuts the at least one rope at longitudinally spaced locations to create intermediate products; and
   drying the intermediate products to form the pet treats.

6. The method of claim 1, further comprising applying one or more coatings to at least one exposed surface of the inner core, wherein the one or more coatings infuse into the inner core.

7. The method of claim 6, wherein the one or more coatings contain at least one bio-active compound.

8. The method of claim 7, wherein the at least one bio-active compound includes heat-labile active ingredients and said one or more coatings is applied after formation of the body.

9. The method of claim 7, wherein the at least one bio-active compound is selected from the group consisting of probiotics, enzymes, antioxidants, antimicrobials, vitamins, a calcium source, flavorings, calcium chelating agents, plant compounds and plant extracts.

10. The method of claim 1, further comprising using rice flour, potato flour, potato starch, gelatin, glycerin, pea starch, cultured whey, cellulose, citric acid and salt in forming the body.

11. A pet dental treat comprising a body with a soft, porous inner core and an outer shell surrounding the porous core, said outer shell being tooth-shaped in cross-section and having integral in-turned retaining elements at an entrance region to a slot extending longitudinally along said body, with the retaining elements defining, at least in part, a pocket of the slot.

12. The pet dental treat of claim 11, further comprising: an edible insert within into the pocket, wherein the edible insert extends past the retaining elements within the pocket and the retaining elements are configured to prevent the edible insert from inadvertently falling out of pocket.

13. The pet dental treat of claim 12, wherein the edible insert comprises a medicinal item, a vitamin, a palatability enhancer, a digestion additive or a mouth surface effective composition.

14. The pet dental treat of claim 13, wherein the edible insert takes the form of a pill, capsule, gummy, or paste.

15. The pet dental treat of claim 11, further comprising one or more coatings provided on at least one exposed surface of the inner core.

16. The pet dental treat of claim 15, wherein the one or more coatings contain at least one bio-active compound.

17. The pet dental treat of claim 16, wherein the at least one bio-active compound includes heat-labile active.

18. The pet dental treat of claim 16, wherein the at least one bio-active compound is selected from the group consisting of probiotics, enzymes, antioxidants, antimicrobials, vitamins, a calcium source, flavorings, calcium chelating agents, plant compounds and plant extracts.

19. The pet dental treat of claim 11, wherein the body is composed of at least rice flour, potato flour, potato starch, gelatin, glycerin, pea starch, cultured whey, cellulose, citric acid and salt.

* * * * *